United States Patent
Schneider

(10) Patent No.: US 6,616,892 B2
(45) Date of Patent: Sep. 9, 2003

(54) PROCESS FOR TREATING ANIMAL HABITATS

(75) Inventor: David J. Schneider, Union, KY (US)

(73) Assignee: H & S Chemical Co. Inc., Covington, KY (US)

( * ) Notice: Subject to any disclaimer, the term of this patent is extended or adjusted under 35 U.S.C. 154(b) by 0 days.

(21) Appl. No.: 09/909,707

(22) Filed: Jul. 20, 2001

(65) Prior Publication Data

US 2003/0024484 A1 Feb. 6, 2003

(51) Int. Cl.⁷ .............................. A61L 2/00; A61L 2/16
(52) U.S. Cl. .................... 422/5; 424/76.6; 47/58.1 R; 119/651
(58) Field of Search ................ 119/651; 47/58.1; 424/405, 76.6; 422/5

(56) References Cited

U.S. PATENT DOCUMENTS

| | | | | |
|---|---|---|---|---|
| 4,306,516 A | * | 12/1981 | Currey | 119/171 |
| 4,369,199 A | * | 1/1983 | Katzen | 426/626 |
| 4,427,630 A | * | 1/1984 | Aibe et al. | 422/122 |
| 4,500,339 A | * | 2/1985 | Young et al. | 106/15.05 |
| 4,728,498 A | * | 3/1988 | Theeuwes | 210/755 |
| 5,814,312 A | * | 9/1998 | Reich et al. | 424/400 |
| 5,906,825 A | * | 5/1999 | Seabrook, Jr. et al. | 424/404 |
| 6,196,156 B1 | * | 3/2001 | Denesuk et al. | 119/28.5 |
| 6,277,344 B1 | * | 8/2001 | Hei et al. | 423/210 |

FOREIGN PATENT DOCUMENTS

| | | | | |
|---|---|---|---|---|
| JP | 52142661 A | * | 11/1977 | B01D/53/34 |

* cited by examiner

Primary Examiner—Charles T. Jordan
Assistant Examiner—Tara M Golba
(74) Attorney, Agent, or Firm—Ronald R. Bahr

(57) ABSTRACT

This invention deals with a process for treating and sanitizing animal habitats. In addition to sanitizing the habitat the production of ammonia and odor from fecal matter and urine is inhibited or terminated. In the process an animal habitat is cleaned and subsequently treated with trichloromelamine (TCM). The TCM may be applied by spraying the habitat with a solution of TCM, by dusting the habitat with powdered TCM or by treating bedding/litter with TCM. This process produces healthier animals and as such the productivity of a given grow out is increased. The process of this invention is particularly suited to animal habitats which are used to raise batches of hogs, cattle, turkeys and chickens on a continuous basis.

40 Claims, No Drawings

PROCESS FOR TREATING ANIMAL HABITATS

FIELD OF THE INVENTION

This invention deals with sanitizing and the improvement of animal habitats wherein the animals are being kept by humans. More particularly this invention is concerned with sanitizing and improving animal habitats in a farming environment in order to provide more productive and healthful animals. In accordance with this invention a wide variety of different habitats can be sanitized and improved. The process of this invention comprises the application of trichloromelamine to the habitat environment which contains or will contain bacteria so as to achieve a specific but relatively low residual concentration of trichloromelamine. The trichloromelamine will sanitize and improve the habitat Further the invention is concerned with ammonia and odor control.

BACKGROUND OF THE INVENTION

In the past trichloromelamine (hereinafter TCM) has been used extensively to sanitize floors, table tops, kitchens and kitchen utensils. This sanitization is usually effected by the spraying of a dilute solution of TCM on to surfaces to be treated or objects such as eating utensils, pots and pans etc. These objects may be likewise soaked in solutions of TCM. Further TCM has been used to kill bacteria on foods by the soaking of food in a solution of TCM such as the soaking of fresh vegetables in a solution of TCM. In these environments the concentration of TCM which can be used is carefully controlled by the E.P.A. and the Food and Drug Administration. This control will be discussed in detail herein below.

Soon after man decided to domesticate animals thousands of years ago, man decided that at least in some circumstances it was desirable to keep domesticated animals in a defined space i.e. keeping fowl in a chicken house or cows in a barn. This keeping of domesticated animals in a defined space resulted in the contamination of the space with fecal matter and urine. This concentration of fecal matter and urine in a confined space results in the space being contaminated with unacceptable levels of bacteria. This bacteria often resulted in the contained animals becoming diseased.

Further this concentration of fecal matter and urine often results in the contamination of the defined space with unhealthy levels of ammonia such that the productivity or health of the contained animal was adversely affected. This fecal matter and urine results in odors which cause troublesome environmental problems.

In modern times the need to provide animals in a habitat with a temperature desirable environment has been recognized. The control of the temperature in animals habitats uses significant energy.

In many cases this energy use is increased when the space in which the animals are confined is vented in order to remove undesirable ammonia. That is as the atmosphere in the habitat is vented new air must be heated or cooled in order to achieve the desired temperature. This process results in increased energy use.

In view of the above points there is a need for a process which will sanitize animal habitats, minimize future ammonia creation, prevent odors and save energy.

In the prior art animal habitats have been treated with aluminum sulfate however these treatments have failed to solve the problems discussed above.

BRIEF DESCRIPTION OF THE INVENTION

The sanitization and control of habitats in which domesticated animals are kept has been a problem which man has addressed since the very beginning of animal domestication. If the habitat in which domesticated animals are kept is not controlled the animals contained can become diseased or their productivity is curtailed.

The containment of animals in a defined space for purposes of domesticating the animals is thousands of years old. This containment of domesticated animals results in unhealthy concentrations of fecal matter and urine. These concentrations can result in bacteria which can cause various maladies disease in the contained animals. Further these concentrations of fecal matter and urine can result in the production of ammonia in unhealthy concentrations such that the contained animals can be asphyxiated. In modern times it has become customary to raise large quantities of animals in batches. The animals in these batches are contained in a defined habitat i.e. a batch of piglets in a hog house or a batch of turkeys in a poultry house. The process of raising a batch of animals to market size is called a grow out.

Prior to starting a new grow out, it is desirable to sanitize the habitat in order to prevent the transfer of diseases from one batch of animals to new batch of animals in a new grow out cycle.

In the past disinfectants such as lime, bleach, formaldehyde etc. have been used. While the disinfectants have some effect on the bacteria they had no effect on the future creation of ammonia or other odors coming from the fecal matter. Further because of its adverse effects, the use of formaldehyde has been banned in many areas.

In accordance with the process of this invention the habitat is treated with a trichloromelamine (TCM) prior to starting the grow out process, treatment during the grow out process may likewise be effected. As a result of this treatment the habitat is sanitized, that is the bacteria are killed and the future production of ammonia during the grow out is inhibited. Because the production of ammonia is inhibited the need to ventilate the habitat in minimized and hence significant energy is saved in that the need to heat or cool new air coming into the habitat is minimized. To put this aspect of the subject invention in other terms by use of the invention the energy consumption of a given animal through the grow out is minimized.

Further the bacteria and ammonia content of the environment is decreased, the animals are healthier in the grow out, and hence the productivity of a batch of animals is enhanced.

The subject invention can be used in connection with all manner of animals i.e. pigs, cows, cattle, ducks, turkeys, chickens etc. Because of the low toxicity of TCM to fowl the process of this invention is particularly suited for use with turkeys and chickens.

OBJECTS OF THE INVENTION

An object of the invention is an effective way to sanitize an animal habitat.

Another object of this invention is a process whereby the production of ammonia from fecal matter and urine is minimized.

Still another of the invention is a process whereby energy might be saved in the production of domesticated animals.

Another object of the invention is a process whereby the productivity of a grow out of a batch of animals is increased.

A further object of this invention is odor control wherein the odors originate from animal habitats.

DESCRIPTION OF THE PREFERRED EMBODIMENT

As per the above discussion the subject invention deals with a process whereby animal habitats can be readily sanitized. Further in accordance with this invention the creation of ammonia from fecal matter and urine is reduced. The subject invention comprises the treatment of an animal habitat with trichloromelamine (TCM) usually prior to starting a new batch of animals in a grow out. The term grow out relates to the placement of a batch of juvenile animals in a defined habitat and feeding the animals until they reach marketable size whereupon they are slaughtered.

The habitat in which the grow out occurs is used over and over. For example a poultry house which is used to raise continuing batches of turkeys or chicken.

In order to prevent the transfer of diseases from one batch of animals to another batch it is imperative that the animal habitat be sanitized after a given batch of animals reaches marketable size and is slaughtered. Traditionally this sanitization has been effected with lime, bleach, formaldehyde etc.

In accordance this invention the habitat is sanitized by treatment with TCM. This treatment may be effected by the dusting of powdered TCM through out the habitat or by treating floor litter with TCM, or it may be effected by soaking the total habitat with a solution of TCM. Mixtures and combination of these methods may also be used. In accordance with the above set forth methods an effective amount of residual TCM is left in the habitat after the sanitizing process is effected.

In a grow out large quantities of fecal matter and urine are deposited in the habitat. The decomposition of fecal matter and urine in the habitat produces ammonia. This ammonia as a gas becomes a part of the atmosphere of the habitat i.e. the concentration of ammonia in the air of a poultry house reaches toxic levels. While animals during a grow out develop a tolerance for this ammonia, regardless of this tolerance the presence of ammonia adversely affects the productivity of a given batch of animals. Further the presence of high concentrations of ammonia makes the animals, and in particular fowl, more susceptible to disease. That is animals that are allowed to breath clean air are healthier, and less stressed and hence they produce more meat. For these reasons it is desirable that the ammonia content of the atmosphere of an animal habitat be kept to a minimum. The raising of poultry in batches is extremely common, if in a poultry house the ammonia level is allowed to reach unacceptable levels the poultry die as a result of airsacculitis.

Regardless of the possibility of death, even if the poultry do not die, if they are less stressed they tend to put on more weight and hence the profit for a given grow out is enhanced.

Even small weight increases such as a one ounce increase over a large batch of poultry, 10,000+birds, can result in a significant profit enhancement.

When ammonia is produced it must be vented out of the habitat in order to prevent the adverse effects discussed above. In order to enhance the production of meat in a grow out it has become common to maintain a desired and pre-selected temperatures in a grow out. This pre-selected temperature will vary from species to species. In order to maintain a given pre-selected temperature energy must be expended. That is the habitat must be heated or cooled in order to maintain the pre-selected temperature.

When ammonia is vented out of the habitat incoming air must be heated or cooled in order that the pre-selected temperature for the habitat is maintained.

In accordance with this invention, it has been found that when the habitat is treated with TCM the production of ammonia is minimized. As a result of this decrease in the production of ammonia, less venting is needed, therefore less energy is needed to maintain the habitat at the pre-selected temperature. Hence the energy consumption of a given animal is decreased.

While the applicant is not sure of how the TCM decreases ammonia production it is hypothesized that the TCM affects the nitrogen bonding or the nitrogen cycle in such a manner that the production of ammonia is decreased. This question will be discussed in greater detail herein below.

The control of the bacteria in a habit affects the health of every part of the animal. In this regard if the bacterial content of the litter in which an animal stands is minimized the animals will have healthier feet. For example if the bacterial content of the litter in which chickens stand is minimized the incidence of footpad dermatitis will be decreased. This makes the crop of chicken feet more valuable in any grow out as chicken feet which are effected with dermatitis are not marketable.

Moving up the animal, the body of an unstressed animal tends to put on weight faster than a stressed animal. A diseased animal is naturally stressed, hence a diseased animal tends to put on less weight when compared to a healthy animal.

Continuing up the animal as is mentioned above the subject invention decreases the production of ammonia in an animal habitat, this decrease in ammonia production has very beneficial and healthful effects on the animals in a grow out i.e. as is mentioned above the presence of excess ammonia in a poultry grow out can kill the poultry as a result of airsacculitis. Further the presence of excess ammonia makes poultry more susceptible to infectious bronchitis and laryngotrachetis. The presence of these diseases further depresses the weight gain of a given fowl.

The subject invention is advantageous in two ways these being in the control of bacteria and in decreasing the production of ammonia from fecal matter and urine. Bacteria which is controlled by the process of the subject invention include, but is not limited to salmonella, *E coli* etc.

Having a collateral way to enhance the health of contained animals is particularly important at the present time as the use of antibodies on animals in a grow out, is being restricted by the FDA. The use of antibodies is being restricted in order to prevent the transfer of resistant strains of bacteria to humans who eat the flesh of the animals that are produced in a grow out.

The fecal matter and urine of the animals contained in the habitat contain substantial quantities of nitrogen bearing compounds. The process of how these nitrogen bearing compounds are converted to ammonia is not fully understood by the applicant. It is felt that the nitrogen bearing compounds may be converted to nitrogen gas $N_2$ which is subsequently converted by nitrogen-fixing bacteria to ammonia.

The applicant speculates that the production of ammonia may be affected by the destruction of the nitrogen-fixing bacteria by the TCM. The destruction of the nitrogen-fixing bacteria by TCM interrupts the nitrogen cycle and thereby prevents the formation of ammonia and hence its release into the atmosphere of the habitat, to the detriment of the animals as may be contained in the habitat.

An initial treatment of a habitat may not be sufficient to impede the production of ammonia from fecal matter and urine throughout the grow out. If this is the case it is within the scope of this invention to retreat the habitat with TCM at an intermediate point in the grow out. In order to slow down the production of ammonia at an intermediate stage of the grow out it is preferred that the litter be retreated with TCM as this brings the TCM into direct contact with the problem area namely the fecal matter urine soaked bedding/litter.

The application of TCM in accordance with this invention has indirect insecticide properties in that by lowering the pH the life cycle of certain insects is interrupted and hence the insect is controlled, i.e. by the application of TCM to a habitat the pH is lowered to less than 5, a point at which the formation and growth of the Darkling beetle will not occur.

The application of the process of this invention is particularly suited to animal habitats that are used to raise continuing batches of animals for meat production i.e. batches of hogs, chickens and turkeys. In addition the process of this invention can be used in conjunction with other aspects of animal habitats such as sanitizing of dairy barns, zoo enclosures and it can be formulated into cat litter and litter for other animals.

Once a grow out is completed there remains in the habitat a large quantity of fecal mater which is mixed with bedding/litter. This composite material must be disposed of in an environmental friendly manner. The process of this invention is advantageous as it facilitates disposal of the bedding and fecal matter in an environmental friendly manner due to its low bacteria content The process of this invention is also advantageous in that when treated in accordance with this invention the habitats are less odorous. The odor control is in addition to the reduction in ammonia as is discussed above. While the applicant is not sure of how this odor control is effected it is felt that the odor control results from the ability of the residual TCM moiety to bond with sulfur and nitrogen bearing molecules. That is when the chlorine is stripped from the TCM molecule an active residual moiety exists. This residual moiety has multiple active sites which can bond with odorous nitrogen and sulfur bearing compounds.

When the habitat is to be sprayed with a solution of TCM in accordance with this invention, it is preferred that the solution be formulated from a dry powder having the composition of Table I. All parts are by weight.

TABLE I

| Monosodium Phosphate | 40 |
| Citric Acid | 28.3 |
| Wetting Agent | 13.00 |
| TCM | 18.70 |
| | 100.00 |

The dry powder was dissolved in water at the rate of 0.25 oz. To 3 gal water to give a concentration of about 100 ppm. The solution was sprayed on to the habitat.

What is claimed is:

1. A process for reducing the production of ammonia and odors in an animal habitat containing fecal matter and urine comprising the steps of treating said habitat with an effective amount of trichloromelamine wherein the application of trichloromelamine is at a point in time wherein it can affect the production of ammonia and odors from nitrogen and sulfur bearing compounds as may be present in the habitat.

2. The process of claim 1 wherein the treatment of the habitat with trichloromelamine is prior to the placement of animals in the habitat.

3. The process of claim 1 wherein the treatment of the habitat with trichloromelamine is after placement of the animals in the habitat.

4. The process of claim 1 wherein the treatment of the habitat with trichloromelamine is prior to and after placement of the animals in the habitat.

5. The process of claim 1 wherein the treatment of the habitat is effected by soaking said habitat with a solution of trichloromelamine.

6. The process of claim 2 wherein the treatment of the habitat is effected by soaking said habitat with a solution of trichloromelamine.

7. The process of claim 3 wherein the treatment of the habitat is effected by soaking said habitat with a solution of trichloromelamine.

8. The process of claim 4 wherein the treatment of the habitat is effected by soaking said habitat with a solution of trichloromelamine.

9. The process of claim 1 wherein the treatment of the habitat with trichloromelamine is effected by dusting with powdered trichloromelamine.

10. The process of claim 2 wherein the treatment of the habitat with trichloromelamine is effected by dusting with powdered trichloromelamine.

11. The process of claim 3 wherein the treatment of the habitat with trichloromelamine is effected by dusting with powdered trichloromelamine.

12. The process of claim 4 wherein the treatment of the habitat with trichloromelamine is effected by dusting with powdered trichloromelamine.

13. The process of claim 2 wherein the treatment with trichloromelamine is effected on bedding/litter as is contained in the habitat.

14. The process of claim 3 wherein the treatment with trichloromelamine is effected on bedding/litter as is contained in the habitat.

15. The process of claim 4 wherein the treatment with trichloromelamine is effected on bedding/litter as is contained in the habitat.

16. The process of claim 7 wherein the treatment with trichloromelamine is effected on bedding/litter as is contained in the habitat.

17. The process of claim 8 wherein the treatment with trichloromelamine is effected on bedding/litter as is contained in the habitat.

18. The process of claim 11 wherein the treatment with trichloromelamine is effected on bedding/litter as is contained in the habitat.

19. The process of claim 12 wherein the treatment with trichloromelamine is effected on bedding/litter as is contained in the habitat.

20. A process for sanitizing an animal habitat comprising the steps of treating said habitat with an effective amount of trichloromelamine wherein the application of the trichloromelamine is done in such a manner as to bring the trichloromelamine into contact with a bacteria as may be present in the habitat.

21. The process of claim 20 wherein the treatment of the habitat with trichloromelamine is prior to placement of the animals in the habitat.

22. The process of claim 20 wherein the treatment of the habitat is after placement of the animals in the habitat.

23. The process of claim 20 wherein the treatment of the habitat with trichloromelamine is prior to and after placement of the animals in the habitat.

24. The process of claim 20 wherein the treatment of the habitat is effected by soaking said habitat with a solution of trichloromelamine.

25. The process of claim 21 wherein the treatment of the habitat is effected by soaking said habitat with a solution of trichloromelamine.

26. The process of claim 22 wherein the treatment of the habitat is effected by soaking said habitat with a solution of trichloromelamine.

27. The process of claim 20 wherein the treatment of the habitat with trichloromelamine is effected by dusting with powdered trichloromelamine.

28. The process of claim 21 wherein the treatment of the habitat with trichloromelamine is effected by dusting with powdered trichloromelamine.

29. The process of claim 22 wherein the treatment of the habitat with trichloromelamine is effected by dusting with powdered trichloromelamine.

30. The process of claim 23 wherein the treatment of the habitat with trichloromelamine is effected by dusting with powdered trichloromelamine.

31. The process of claim 20 wherein the treatment with trichloromelamine is effected on bedding/litter as is contained in the habitat.

32. The process of claim 21 wherein the treatment with trichloromelamine is effected on bedding/litter as is contained in the habitat.

33. The process of claim 22 wherein the treatment with trichloromelamine is effected on bedding/litter as is contained in the habitat.

34. The process of claim 23 wherein the treatment with trichloromelamine is effected on bedding/litter as is contained in the habitat.

35. The process of claim 24 wherein the treatment with trichloromelamine is effected on bedding/litter as is contained in the habitat.

36. The process of claim 25 wherein the treatment with trichloromelamine is effected on bedding/litter as is contained in the habitat.

37. The process of claim 26 wherein the treatment with trichloromelamine is effected on bedding/litter as is contained in the habitat.

38. The process of claim 27 wherein the treatment with trichloromelamine is effected on bedding/litter as is contained in the habitat.

39. The process of claim 28 wherein the treatment with trichloromelamine is effected on bedding/litter as is contained in the habitat.

40. The process of claim 29 wherein the treatment with trichloromelamine is effected on bedding/litter as is contained in the habitat.

* * * * *